United States Patent
Fields

[19]

[11] Patent Number: 6,086,365
[45] Date of Patent: Jul. 11, 2000

[54] BONDED INTERMAXILLARY FIXATION SPLINT

[75] Inventor: R. Theodore Fields, Rowlett, Tex.

[73] Assignee: Walter Lorenz Surgical, Inc., Jacksonville, Fla.

[21] Appl. No.: 09/017,449

[22] Filed: Feb. 2, 1998

[51] Int. Cl.[7] .................................................. A61C 3/00
[52] U.S. Cl. ........................................... 433/18; 433/215
[58] Field of Search .................................. 433/9, 18, 19, 433/24, 215

[56] References Cited

U.S. PATENT DOCUMENTS

| | | | |
|---|---|---|---|
| 3,348,311 | 10/1967 | Weissman | 433/18 |
| 3,474,779 | 10/1969 | Wall, Jr. | 433/18 |
| 3,675,327 | 7/1972 | Huget et al. . | |
| 4,015,334 | 4/1977 | Moss | 433/24 |
| 4,068,379 | 1/1978 | Miller et al. . | |
| 4,090,299 | 5/1978 | Williams | 433/18 |
| 4,165,561 | 8/1979 | Miller et al. . | |
| 4,202,328 | 5/1980 | Sukkarie . | |
| 4,230,104 | 10/1980 | Richter . | |
| 4,533,320 | 8/1985 | Piekarsky . | |
| 4,752,221 | 6/1988 | Hanson et al. . | |
| 4,904,188 | 2/1990 | Baurmash | 433/215 |
| 4,952,142 | 8/1990 | Nicholson . | |
| 5,087,202 | 2/1992 | Krenkel | 433/215 |
| 5,098,304 | 3/1992 | Scharf | 433/215 |
| 5,110,290 | 5/1992 | Wong . | |
| 5,184,955 | 2/1993 | Baer et al. | 433/215 |
| 5,230,619 | 7/1993 | Wong . | |
| 5,232,361 | 8/1993 | Sachdeva et al. . | |
| 5,256,062 | 10/1993 | Griott . | |
| 5,263,859 | 11/1993 | Kesling . | |
| 5,593,303 | 1/1997 | Cohen et al. . | |
| 5,613,853 | 3/1997 | Chasan et al. | 433/215 |
| 5,842,856 | 12/1998 | Casey | 433/19 |

FOREIGN PATENT DOCUMENTS

| | | | |
|---|---|---|---|
| 1678354 | 9/1991 | U.S.S.R. | 433/18 |
| 2110093 | 6/1983 | United Kingdom | 433/24 |

OTHER PUBLICATIONS

Walter Lorenz Surgical Instruments, Lorenz–Barmesh Arch Bar Bonding Kit Brochure, Copyright 1990.

*Primary Examiner*—Ralph A. Lewis
*Attorney, Agent, or Firm*—Harness, Dickey & Pierce, P.L.C.

[57] ABSTRACT

Fracture reduction and intermaxillary fixation are performed with a dental splint that is directly bonded by cement to the teeth of a patient for temporarily fixing and immobilizing the patient's jaws during and following oral surgery. The splint includes an arch band having a back side surface for receiving a deposit of bonding cement and a facial side surface from which multiple ligature studs project for engaging ligature wires. Each stud includes a tapered shank portion and a symmetrical head portion. The head portion of each stud is conformed for pivotal coupling engagement with a forceps tool. The arch band is intersected by multiple flow passages that permit bonding cement deposited on the back side surface of the arch band to flow or extrude onto the facial side surface as the arch band is pressed against the patient's teeth. Symmetrical construction of the head portions allows universal coupling engagement and manipulation by installation and de-bonding tools.

32 Claims, 4 Drawing Sheets

BONDED INTERMAXILLARY FIXATION SPLINT

BACKGROUND OF THE INVENTION

This invention relates generally to reconstructive oral surgery, and in particular to intermaxillary fixation devices used in the restoration and healing of maxillo-mandibular injuries, including the reduction and temporary fixation of teeth, teeth rows and jaw segments.

According to current practice, fractures of the lower jaw (mandible), the upper jaw (maxilla) and some wounds resulting from surgical intervention to correct abnormalities or to remove tumors, involve reduction and re-alignment of fracture segments followed by passive fixation of the lower and upper rows of teeth in the maximum intercuspation position. Oral and maxillo-facial surgeons, plastic surgeons, and otolaryngologists routinely wire the jaws together (intermaxillary fixation) to achieve reduction and maintain fixation during and following oral surgery.

The conventional procedure of wiring the jaws together is performed with a temporary splint in which two or more arch bars are attached to the patient's teeth by circumdental wires. The arch bars are cut to the appropriate lengths and are secured by the circumdental wires which are looped tightly around the teeth. The upper and lower jaws are drawn together by tightening inter-arch wires that are looped around hooks carried on each arch bar. The fracture segments are then manually guided into alignment as the inter-arch wire loops are tightened, until proper reduction and fixation have been established.

The attachment of an arch bar by a circumdental wire loop is detrimental to proper gingival health maintenance. The circumdental wires penetrate and blunt the papilla. Moreover, the circumdental wire loops intrude within the gingival sulcus where plaque accumulation begins, and thus hinder hygienic access. The resulting gingival penetration is the cause of inflammation as well as discomfort.

The handling and manipulation of circumdental wires during attachment of an arch bar places the surgeon at an intra-operative risk of skin penetration. Double gloving is used for increased protection, but decreases operator dexterity and does not guarantee safety. Obviously, the elimination of circumdental wires would substantially reduce the surgeon's risk to stick penetration.

Because of such risks and limitations, improvements in arch bar construction have been proposed in which acid-etch and direct cement bonding techniques are used for attaching the arch bars to teeth without utilizing circumdental wires. For example, Baurmash U.S. Pat. No. 4,904,188 discloses an arch bar that includes integrally formed ligature hooks and a layer of a metallic mesh material that is spot-welded onto the back surface of the arch bar for forming an adhesive bonding attachment to tooth enamel. The upper and lower arch bars carry upwardly turned and downwardly turned ligature hooks, respectively, for engaging intermaxillary ligature wires.

Krenkel U.S. Pat. No. 5,087,202 discloses a stabilizing splint that is bondable onto tooth enamel, the splint including a series of rings interconnected by bar segments, with adhesive being deposited into the bore of each ring. Intermaxillary fixation wires are engaged by upwardly and downwardly turned hooks.

Baehr U.S. Pat. No. 5,184,955 discloses a similar arrangement in which bonding rings are slidably mounted onto a metal arch wire. Upper and lower arch wires are connected together by interarch ligature wires.

U.S. Pat. No. 4,202,328 discloses an arch bar in the form of a flexible metal arch bar that is secured onto a row of teeth by a circumdental wire and retainer beads that project between adjacent teeth. Upper and lower arch bars carry oppositely turned hooks for engaging fixation wires.

U.S. Pat. No. 5,613,853 discloses another splint arrangement for stabilizing a row of teeth in which an arch bar is secured onto a tooth by a plastic tie cable that encircles the tooth and the arch bar. Interarch cable ties are also secured by upwardly and downwardly turned hooks carried on upper and lower arch bars, respectively.

U.S. Pat. No. 4,230,104 discloses yet another arch bar splint in which the arch bar is secured in place by circumdental wires that are looped around individual teeth. Intermaxillary fixation wires are secured by upwardly turned and downwardly turned tabs.

U.S. Pat. Nos. 4,068,379 and 4,165,561 to Miller et al disclose a metallic mesh or metallic foil base pad for use in combination with cement for bonding an orthodontic bracket onto tooth enamel.

U.S. Pat. No. 4,752,221 discloses an orthodontic bracket having a thin porous layer of sintered metal powder as a cement bonding base.

U.S. Pat. No. 5,110,290 discloses a metallic mesh screen forming a cement bonding layer for attaching an orthodontic bracket onto tooth enamel.

U.S. Pat. No. 5,256,062 discloses a non-metallic appliance formed from a transparent material such as crystalline alumina, together with a stainless steel metallic foil mesh bonding pad for adhesively bonding the transparent appliance onto tooth enamel.

U.S. Pat. No. 4,952,142 discloses light curable polymer bonding compounds in combination with a mesh bonding layer for attaching an orthodontic appliance onto tooth enamel.

U.S. Pat. No. 5,232,361 discloses an orthodontic bracket constructed of titanium and titanium-based alloys for supporting an orthodontic arch wire. The bracket includes a base portion that is adapted for adhesive bonding attachment to tooth enamel.

The Bauermash arch bar disclosed in U.S. Pat. No. 4,904,188 is typical of conventional arch bar designs in which oppositely turned hooks are attached to lower and upper arch bars for engaging intermaxillary fixation wires. According to that design, the tension forces applied through the intermaxillary fixation wires are primarily applied in only one direction, that is, in a direction opposite to the direction that the hooks are turned from the arch bar. A limitation on that arch bar design is that the interarch wires can easily slip off of the hooks and can also be cut by shearing engagement against the side edge portions of the hooks when the fixation wires are routed transversely with respect to the hooks, especially in a direction that is parallel to the longitudinal axis of the arch bar.

Moreover, the conventional upwardly and downwardly turned hook arrangements are intended for top-to-bottom tightening, and are not suitable for engaging transfracture wires in which substantial forces are applied between right and left jaw segments to obtain reduction. A further limitation on the use of conventional arch bars with integrally formed hooks is that the hooks are as thin as the arch bar itself and are flexible. Because of this flexibility, the hooks often bend and warp as the fixation wires are tightened. Consequently, when bending and warping occur, the hooks must be reshaped and it is sometimes necessary to retighten the ligature wires to maintain proper reduction and fixation.

A further limitation on the use of oppositely turned hooks for securing interarch ligature wires is the difficulty in engaging a gripping tool such as forceps to seize the hook and apply appropriate forces during application or debonding. Such hooks, of course, are not intended for debonding or engagement with conventional forceps, and so it is necessary for the surgeon to manually apply finger pressure against the arch bar during installation. This exposes the surgeon to risk of skin cut or puncture as a result of engagement against a sharp edge. Additionally, the arch bars become contaminated with the powder that is commonly applied to the surgeon's gloves, and such contamination can corrupt the cement bonding agent, resulting in reduced bond strength and premature bonding.

A further limitation on conventional arch bar arrangements that utilize direct adhesive bonding attachment of arch bars to tooth enamel is that such bonds are largely mechanical and initially require an acid-etch of the tooth enamel. The acid-etch step creates undercuts in the tooth enamel or the tooth dentin which increases the bonding surface area. After the hard surface of the tooth has been undercut, a liquid primer and a liquid adhesive are applied and cured, with the cured surface being mechanically interlocked with the undercut structure and bondable with adhesive. This acid-etch offset bonding arrangement provides a high strength, durable bond that is intended for long-term (typically 12 months or more) applications, as commonly employed in the attachment of orthodontic brackets. However, the debonding of such high strength bonding arrangements has resulted in enamel fracture and difficulty in complete removal of the brackets and adhesives from the teeth.

Moreover, the high strength acid-etch bond is achievable only by first obtaining a dry tooth surface. A dry tooth surface is difficult to obtain in practice, since the fracture zone is almost always bordered by moisture producing lacerations and soft tissue avulsions. An additional consideration in the use of conventional acid-etch adhesive bonding is that such cement compositions are formulated for long-term applications, for example the attachment of orthodontic brackets that typically remain on the teeth for twelve months or longer, and must provide long-lasting high bond strength. Most intermaxillary arch bars are designed to remain in place rarely longer than eight weeks, and in some instances the arch bars are used intra-operatively for only a few hours. Moreover, because of the high bond strength of acid-etched composite adhesive bonds, the tooth enamel can be fractured and removed along with the arch bars during debonding. Debonding of such high strength bonds requires the application of a powered handpiece, and some tooth enamel may be sacrificed as the cement residue is abraded from the tooth surface.

BRIEF SUMMARY OF THE INVENTION

The dental splint of the present invention uses interarch ligature wires and arch bands that are attached to a patient's teeth by direct cement bonding for fixing and temporarily immobilizing the patient's jaws during and following oral surgery. The arch bands, preferably made of titanium, are bendable to conform to the facial side surfaces of the patient's teeth. Multiple ligature studs project from the facial side of each arch band for engaging interarch ligature wires.

Each arch band is intersected by multiple apertures that form flow passages through the band. According to this arrangement, bonding cement on the back side surface of the arch band flows or extrudes through the open flow passages onto the facial side surface when the arch band is pressed against the patient's teeth. This produces multiple retainer plugs that are exposed for accelerated curing, and a retainer cap or shoulder overlaps the facial side surface bordering each aperture. The retainer plugs and caps mechanically strengthen the attachment of the cement layer to the arch band.

Each ligature stud includes a tapered shank portion for engaging a ligature wire and a symmetrical head portion for engaging a forceps tool. The symmetrical stud construction accommodates the application of transfracture wires for reducing a fracture, the application of intermaxillary fixation wires to bring the lower and upper rows of teeth into the maximum intercuspation position, universal coupling engagement with de-bonding forceps, and multiple stud engagement with installation forceps and handles.

The arch bands are bonded directly to tooth enamel by a hybrid cement composition that produces a chemical bond with moist tooth enamel as well as a chemical bond with the arch band. The bond that results has an intermediate strength that is intended for relatively short term applications, and can be established without performing an acid-etch. In the preferred embodiment, the hybrid cement composition includes a light-curable resin mixed with a glass ionomer adhesive. The hybrid adhesive does not require an acid-etch prepared surface, and bonds directly to tooth enamel in the presence of moisture.

BRIEF DESCRIPTION OF THE DRAWING

The accompanying drawing is incorporated into and forms a part of the specification to illustrate the preferred embodiments of the present invention. Throughout the drawing, like reference numerals designate corresponding elements. This drawing, together with the description, serves to explain the principles of the invention and is provided only for the purpose of illustrating exemplary embodiments showing how the invention can best be made and used. The drawing should not be construed as limiting the invention to the illustrated and described embodiments. Various advantages and features of the invention will be understood from the following detailed description taken in connection with the appended claims and with reference to the attached drawing figures in which:

DETAILED DESCRIPTION OF THE INVENTION

Figure 1:
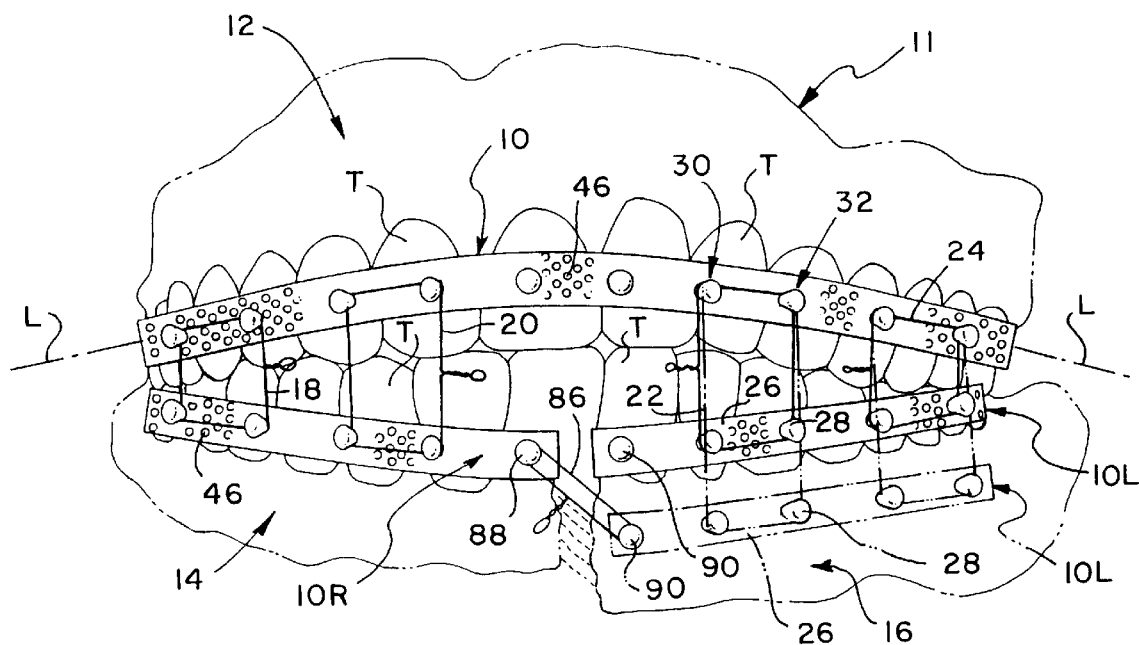
FIG. 1 is a perspective view illustrating the reduction of a mandibular fracture and intermaxillary fixation using the dental splint assembly of the present invention.

Preferred embodiments of the invention are described herein with reference to various examples of how the invention can be made and used. Like reference numerals are used throughout the description and several views of the drawing to indicate like or corresponding parts.

Figure 2:
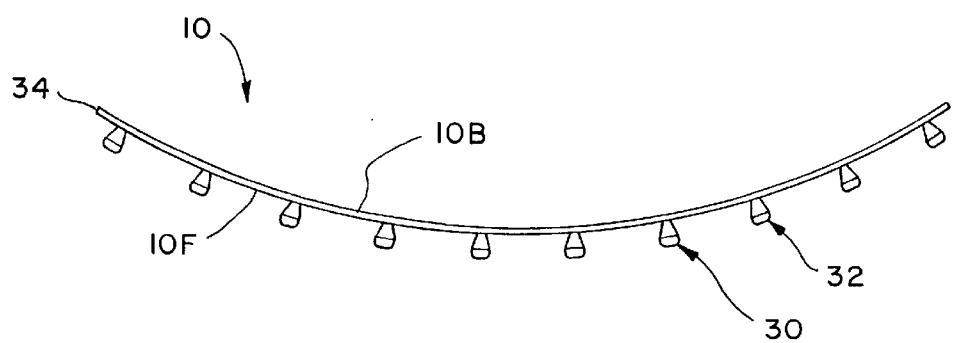
FIG. 2 is a top plan view of an arch band which forms a part of the dental splint of FIG. 1.

Referring now to FIG. 1 and FIG. 2, the dental arch band 10 of the present invention forms a part of a dental splint assembly 12 for the restoration and healing of a maxillo-mandibular injury. In this exemplary embodiment, the lower jaw has been fractured into segments 14, 16 and the dental splint assembly 12 includes an arch band 10 attached to the teeth T of the upper jaw 11, an arch band 10A attached to the teeth T of the lower jaw segment 14, and an arch band 10B attached to the teeth T of the lower jaw segment 16.

Although a fracture of the lower jaw is illustrated, the arch band 10 and the dental splint assembly 12 of the present invention can be used for restoring fractures of the upper jaw, and fractures of both jaws. Another application includes the restoration of wounds resulting from surgical intervention to correct abnormalities or for tumor access or removal from the jaws, the face or even the cranial base. Additionally, the arch band and dental splint assembly can be used for patients that have a dislocated jaw and cannot interdigitate their teeth properly. In such cases, a short period of intermaxillary fixation is applied to permit muscle spasms to subside.

In patients with upper or lower jaw fractures, the affected jaw may be deviated to the left or to the right and there are situations where such patients are not able to return the jaw to the proper position. These patients are anesthetized during surgery, and the affected jaw is manipulated into the proper position with the lower and upper rows of teeth engaged in the maximum incuspation position. The dental splint assembly 12 is attached to the patient's teeth temporarily to maintain the reduced, fixed position. The splint assembly may be maintained intraoperatively for additional surgical procedures such as the application of bone plates and screws, or it may be maintained for several weeks while the bone segments grow together and the wound heals.

The arch band 10 is directly bonded to the tooth enamel by a hybrid cement that produces a chemical bond with the tooth enamel and arch band while also forming a mechanical interlock the arch band. The upper arch band 10 and the lower arch bands 10A, 10B are cut to the appropriate lengths and are then directly bonded onto tooth enamel as illustrated in FIG. 1. The upper and lower jaws are drawn together by tightening inter-arch ligature wires 18, 20, 22 and 24 that are looped around adjacent ligature studs 26, 28 that project from the lower arch band 10A and ligature studs 30, 32 that project from the upper arch band 10.

The arch bands 10, 10L and 10R each have a facial side surface 10F and a back side surface 10B forming major side surfaces of a substantially flat, rectangular body 34 of compliant, bendable material, preferably titanium or some other corrosion-resistant bio-compatible metal such as stainless steel. In this exemplary embodiment, the flat, rectangular arch band body has a thickness dimension of from about 0.2 mm to about 0.6 mm, a width dimension of from about 3 mm to about 6 mm, and a length dimension that is typically 8 cm to about 10 cm for the upper arch band 10. The lower arch band segments 10R and 10L are cut to an appropriate length for each segment that extends from the fracture line to the terminal tooth of the fracture segment.

Figures 3, 4:
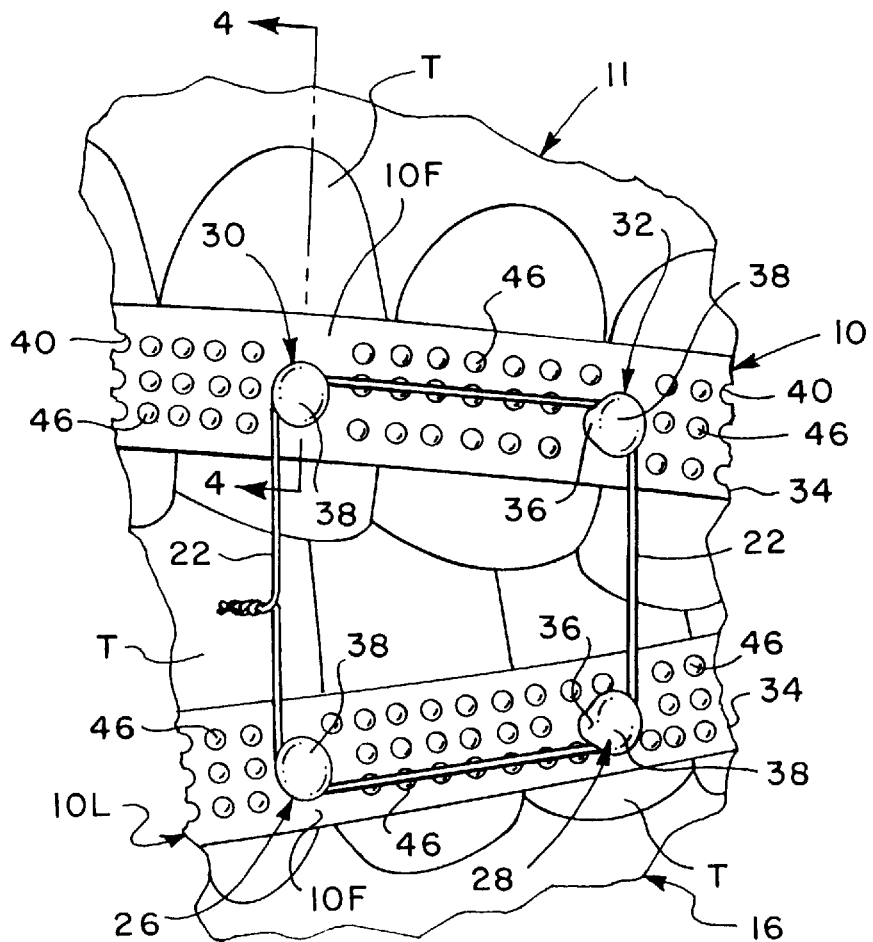
FIG. 3 is a front elevational view, partially broken away, showing details of intermaxillary fixation.
FIG. 4 is a sectional view taken along the line 4—4 of FIG. 3.

Referring now to FIG. 2, FIG. 3 and FIG. 4, each ligature stud includes a shank portion 36 attached to the arch band body 34 and a head portion 38 attached to the shank. Preferably, multiple ligature studs are attached to each arch band and project transversely, preferably orthogonally, with respect to the plane of the facial side surface 10F. In the preferred embodiment, the ligature studs are attached to the facial side surface 10F of the arch band by welding. Alternatively, the ligature studs can be attached to the arch band by soldering. Moreover, each ligature stud can be formed as an integral part of the arch band, for example in an alternative embodiment in which the arch band and the ligature studs are integrally formed of a molded plastic material. In an all-metal integral embodiment, the ligature studs and the arch band are machined from a block of metal stock.

Referring now to FIG. 2 and FIG. 4, the shank portion 36 of each ligature stud slopes inwardly from the head portion 38 to the facial side surface of the arch band, thereby forming an acute angle with the longitudinal axis Z of the stud (FIG. 4). Each shank is tapered towards its union with the arch band so that as the interarch ligature wires are tightened, the wires are pulled against the arch band itself. This allows the shear forces applied to the arch band to be minimized as the interarch wires are tightened so that the risk of premature debonding of the arch band from the tooth surfaces is minimized.

Note in FIG. 4 that the ligature wire 22 is drawn tightly into engagement against the arch band facial surface 10F as well against the tapered shank 36. If the interarch ligature wire 20 were to be laterally offset from the arch band as taught by Bauermash U.S. Pat. No. 4,904,188, a moment force would be created that would tend to pull the ligature stud and band away from the tooth T. The resulting shear force could weaken the bonding strength and prematurely de-bond the arch band from the teeth. By engaging a continuous taper towards the arch band, as the wire 20 is tightened, the wire slides along the tapered shank 36 into engagement with the facial surface 10F of the arch band, thereby virtually eliminating its offset and any resulting moment that could have a debonding effect.

Referring again to FIG. 1 and FIG. 3, each arch band is intersected by multiple apertures 40 that form flow passages through the body 34 of each arch band. According to this arrangement, bonding cement 42 applied to the teeth or to the back side surface of the arch band 10 flows or is extruded through the open flow passages 40 onto the facial side surface 10F when the arch band is pressed against the patient's teeth. This produces multiple retainer plugs 42 that are exposed for accelerated and thorough curing and which form an overlapping annular cap or shoulder 44 around each aperture. When cured, the retainer plugs and caps mechanically interlock and strengthen the bond between the cement layer 42 and the body 34 of the arch band 10.

According to an alternative embodiment, the arch band is a mesh body of interlocking metal links with mesh passages formed between the interlocking metal links, thereby permitting bonding cement 42 contacting the back side surface of the band to flow or extrude into the mesh passages when the arch band is pressed against the patient's teeth. The mesh body is preferably formed of titanium metal and has length, width and thickness dimensions within the ranges specified above.

The arch bands 10, 10R and 10L are bonded directly to tooth enamel by a hybrid cement 42 that produces a chemical bond with moist tooth enamel as well as with the arch band body 34. The chemical bond with the tooth enamel has an intermediate strength that is intended for relatively short-term applications and can be established without performing an acid-etch. In the preferred embodiment, the hybrid cement 42 is a mixture of a light-curable resin and a glass ionomer. The preferred hybrid formulation consists essentially of polyacrylic acid, a light-curable monomer resin and an activator mixed together in an aqueous solution, and a powder of finely ground fluoroalumino-silicate glass crystals. The glass crystals are manually mixed or machine triturated with the aqueous solution until the glass crystals are thoroughly coated. The acid initiates the dissolution of the glass crystals, thus releasing ions which enable chemical bonding.

The resulting hybrid adhesive mixture does not require acid etching, since it establishes a chemical bond to the tooth surface. The bond strength of the hybrid adhesive is not as strong as that of a conventional acid-etch resin bond. The intermediate bond strength permits easy debonding of the arch band and also permits simple removal of the adhesive from the tooth surface. In most cases, the arch band and the cement layer can be completely removed with debonding forceps and a conventional dental scaler, and do not require high speed hand-piece abrading.

One advantage of using the hybrid cement 42 relates to the release of fluoride. The glass ionomer component releases a fluoride-containing agent that prevents demineralization of the tooth surface, thereby preventing the formation of white decalcification spots.

An important aspect of the hybrid adhesive 42 is that it is capable of forming a chemical bond with tooth enamel in the presence of moisture. This is highly desirable since it is very difficult to maintain a dry environment in a typical fracture. The conventional resins used in restorative dentistry have required an absolutely dry field. Any moisture contamination inhibits resin/enamel bonding. In contrast, the glass ionomer component ideally bonds in a moist environment, and the moist tooth surface may increase the strength of the hybrid adhesive bond.

An intermediate bond strength is preferred for attaching the arch band of the present invention, as compared with the relatively high bond strength developed by conventional resins of the type used for acid-etch bonding of orthodontic brackets. Traditional orthodontic bond strengths are higher than desirable for the present arch band application because the orthodontic bracket is relatively small, is applied to a single tooth and is intended for long-term service. The arch wire that is placed through the slot of the orthodontic bracket is designed to apply substantial forces to the individual bracket and high bond strength must be maintained to avoid premature debonding. However, with the arch band of the present invention extending around and over all or nearly all of the teeth, the effective bonding force is the cumulative total applied to all of the teeth. Consequently, a high bond strength for each individual tooth is not required or even desirable, thus simplifying debonding and removal.

An additional consideration is that conventional orthodontic brackets often remain on the teeth for a year or more. The arch band 10 of the present invention is designed for short-term temporary use, rarely for periods exceeding eight weeks. Consequently, high bond strengths are not desirable.

The glass ionomer component requires approximately five to seven minutes to thoroughly cure, whereas the light-curable resin component can be cured in response to the application of intense blue or ultraviolet light in about twenty seconds. By the time the arch band 10 has been bonded to each tooth, the glass ionomer component is substantially cured.

Conventional dental resins (not glass ionomers) can provide up to about twenty-six megapascals of mean shear bond strength. This is approximately equivalent to the cohesive bond strength of the tooth structure itself. Consequently, there is a possibility of tooth fracture occurring as well as an adhesive failure at the tooth/adhesive interface. In contrast, the hybrid adhesive mixture of the present invention provides at most about twenty megapascals of mean shear bond strength and preferably about sixteen megapascals. This reduced bond strength level is more than adequate to resist the intermaxillary fixation wire forces and transfracture wire forces without the risk of fracturing tooth enamel.

Moreover, the intermediate bond strength is not so high as to interfere with debonding, with little if any cement residue remaining on the tooth surface after debonding of the dental splint. One of the reasons that a reduced level of bond strength per tooth is sufficient is because the bond is distributed over a much larger surface area and over multiple teeth as opposed to the bond strength required for a traditional long-term orthodontic bracket that is attached to a single tooth. A bond strength in the range of from about eight megapascals to about twenty megapascals is preferred so that accidental intra-operative and post-operative debonding do not occur.

According to another aspect of the invention, the proportions of the light-curable resin component and the glass ionomer component are varied to provide an intermediate range of bond strengths that are suitable for use with the arch band of the present invention, and which can be easily debonded. Preferably, the hybrid cement composition preferred for use with the arch band 10 provides a bond strength in the range of from about eight megapascals to about twenty megapascals, with a preferred bond strength of about sixteen megapascals. A bond strength in this intermediate range is more than adequate to resist the intermaxillary fixation wire forces and transfracture wire forces, but the level is not so high as to interfere with debonding and removal of cement from the tooth surface. A suitable glass ionomer hybrid adhesive having customer-specified mean shear bond strength can be purchased from GC America Inc. of Chicago, Ill.

The composite cement mixture 42 is prepared by mixing the glass ionomer crystals with the aqueous solution. The mixture is spatulated or triturated to produce a creamy consistency. The ideal consistency is approximately that of gel toothpaste where it is more viscous than water, but less viscous than wax. Essentially, the preferred viscosity is comparable to the viscosity of molasses or honey at 70° F. The mixed cement then may be dispensed from a syringe applicator onto the back side surface 10B of the arch band, or directly onto the tooth enamel.

After the hybrid cement mixture 42 is applied, the arch band 10 is manually placed against the row of teeth as shown in FIG. 1, FIG. 3 and FIG. 4. Cement material 42 flows or extrudes through the apertures 40, thus producing the retainer plugs 44 and caps 46. The conventional resin component of the hybrid cement mixture 42 can be accelerated and cured with high intensity blue light, with curing being achieved in only twenty to forty seconds. Blue or ultraviolet light from a hand instrument is then directed onto the exposed retainer plugs 44 and caps 46, which thoroughly cure within twenty to thirty seconds. By the time the retainer plugs and caps have been cured over each tooth, the glass ionomer component of the hybrid cement mixture is substantially set. The surgeon can then be quite certain that adequate bonding strength has been achieved that will safely react the forces arising during the application of intermaxillary fixation wires and transfracture fixation wires.

In this arrangement, a chemical bond and a mechanical bond are formed between the hybrid cement layer 42 and the arch band, and a chemical bond is formed between the hybrid cement and the tooth surface. The retainer plugs 44 and caps 46 mechanically lock the adhesive layer 42 onto the arch band. This mechanical retention alone provides a strong bond to the arch band.

Referring again to FIG. 2, FIG. 3 and FIG. 4, the shank portion of each stud has a longitudinal axis Z, and the head portion 38 of each stud is symmetrically formed with respect to the longitudinal axis. The head portion of each stud is conformed for engaging a forceps tool, for example the forceps 48 or the forceps 50 shown in FIGS. 5 and 6, respectively. The forceps tool 48 includes gripping jaws or beaks 52, 54. Coupling pockets 56, 58 are formed within beak portions of the gripping jaws.

In the preferred embodiment, the head portion 38 of each stud is conformed for rotational engagement against the gripping jaws within the coupling pockets, thereby permitting pivotal movement and/or rotational movement of the forceps tool relative to the ligature stud. This permits forces applied by the forceps tool during installation and removal of the dental arch band 10 to be directed through a range of angles relative to the stud 36 without slippage of the forceps tool or inadvertent disengagement of the forceps tool from the head portion.

Figure 5:
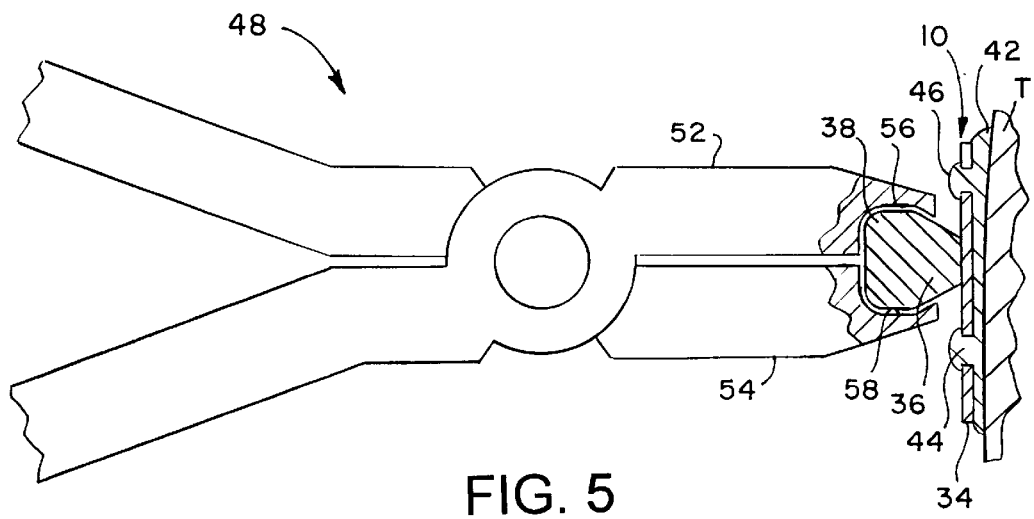
FIG. 5 is an elevational view, partly in section, illustrating capture of a ligature stud by a forceps tool.
Figure 6:
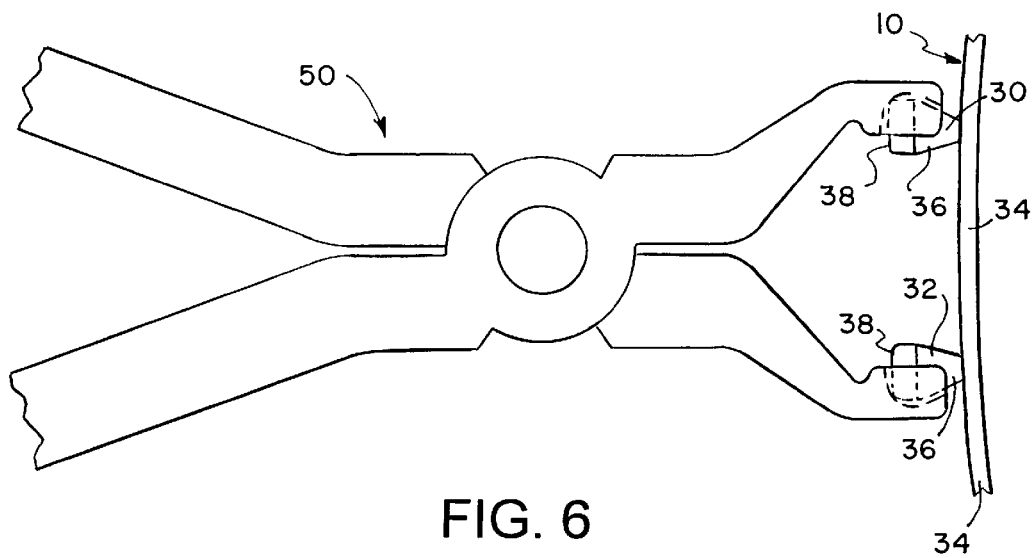
FIG. 6 is a elevational view similar to FIG. 5 illustrating capture of adjacent ligature studs by a forceps tool.

In the preferred form, the head portion 38 of each stud is dome-shaped and the shank portion 36 is conical. Alternatively, the head portion of each stud is hemispherical, as shown in FIGS. 1 and 2. According to another arrangement, the head portion of each stud is cylindrical, as shown in FIGS. 5 and 6. In each embodiment, the head portion is conformed for capture engagement within the coupling pocket of a forceps tool or applicator tool.

Preferably, the head portion of each stud is curved and symmetrical with respect to the shank axis Z wherein the head portion can be captured within the coupling pockets 56, 58 of the forceps 48, thereby permitting rotational engagement of the head against the gripping jaws. When the head portion is hemispherical or dome-shaped, this allows universal pivotal movement of the forceps tool relative to the ligature stud, thus permitting forces to be applied through a wide range of angles relative to the stud during installation, and more importantly, during debonding. Moreover, capture engagement of the head within the forceps coupling pocket prevents slippage of the forceps tool relative to the stud, and prevents inadvertent disengagement of the forceps tool from the head.

Figure 7:
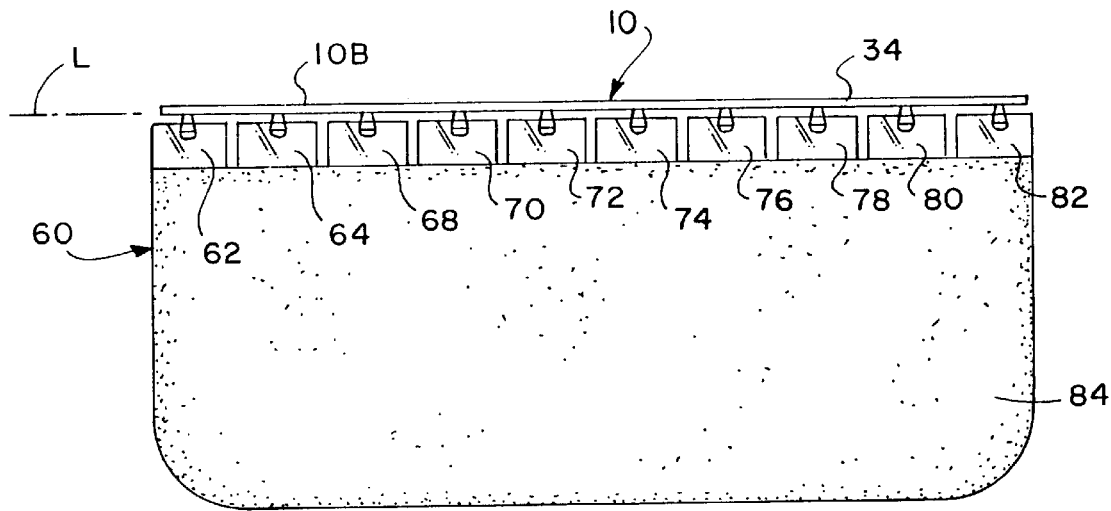
FIG. 7 is a top plan view of an installation handle that has pre-formed sockets for engaging ligature sockets; and, FIG. 8 is a top plan view which illustrates coupling engagement between the ligature studs of the arch band shown in FIG. 2 with the installation handle shown in FIG. 7.
Figure 8:
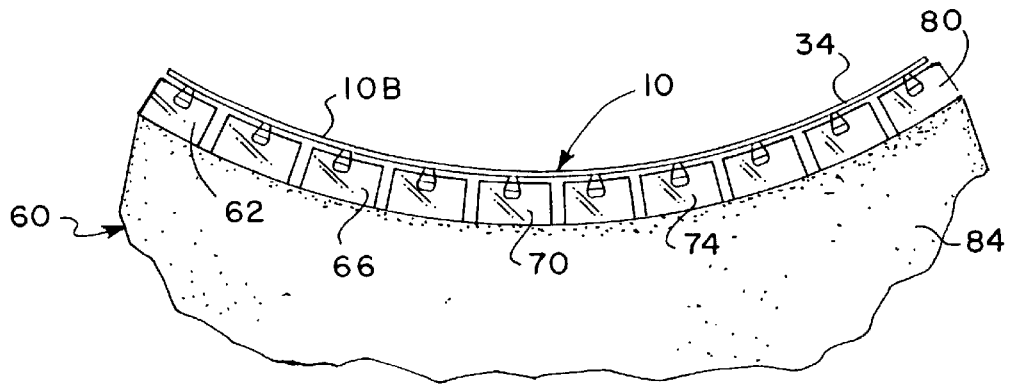

Although the dome-shaped hemispherical head configuration as shown in FIGS. 1, 2 and 3 is preferred, the cylindrical head configuration shown in FIGS. 4, 5 and 6 can be used to good advantage. Each head configuration can be used in combination with the forceps tool 48, 50 as shown in FIGS. 5 and 6, as well as with the manually operated installation handle tool 60 as shown in FIGS. 7 and 8.

Referring again to FIGS. 1 and 2, the arch band 10 has a longitudinal axis of symmetry L, and the ligature studs 30, 32 are located on and are spaced evenly apart along the longitudinal axis of symmetry. This provides top-to-bottom symmetry which allows the arch band to be installed upside down (inverted) as well as right side up.

The alignment of the ligature studs along the longitudinal axis of symmetry on each arch band also permits the ligature studs to be inserted into press-fit sockets 62, 64, 66, 68, 70, 72, 74, 76, 78, 80 and 82 that are formed along the applicator side of the handle 60. The sockets are conformed for press-fit, releasable engagement with the stud head portions 38. Preferably, the sockets are constructed of a resilient, durable material, such as nylon, with each socket being dimensioned for a tight interference fit with the stud head portions. Moreover, the handle 60 includes a stretchable, flexible hand-grip portion 62 that can be stretched to permit the arch band 10 to be flexed and curved as necessary to conform with the patient's teeth. The hand-grip portion is preferably constructed of a stretchable rubber material, and the sockets 62–82 are constructed of a hard, clear plastic material.

A transparent socket body is preferred to permit blue or ultraviolet light to be directed onto the exposed adhesive retainer plugs and caps. The stretchable hand-grip assembly permits the surgeon to apply the layer of cement and accurately position the arch band onto the patient's teeth without touching or otherwise handling the arch band itself. It also permits the surgeon or his assistant to maintain uniform pressure against the arch band as the adhesive is cured. That is, after the cement is deposited on the back side of the arch band, the stretchable applicator 60 can be gripped with both hands, and the arch band assembly can be held in place and appropriate pressure can be maintained during the twenty to thirty seconds that are required for the application of ultraviolet light to the exposed cement plugs. The arch band 10 becomes securely attached in its desired location during the time it takes for the glass ionomer adhesive component to completely cure. Because it is not necessary for the surgeon to touch the arch band, the arch band can be manipulated without contaminating the adhesive deposit with powder from the surgeon's gloves, and also avoids adhesive bonding of the surgeon's gloves with the arch band.

The rubber handle 84 and the hard plastic sockets can be molded in a double durometer mold in which the stretchable handle portion has a soft, flexible durometer and the socket portions have a relatively hard durometer. The socket cavities are finished and hardened so that the stud head portions 38 can be inserted and withdrawn repeatedly without stripping the socket. Preferably, the sockets are transparent so that all of the head portions are visible and full insertion can be confirmed visually, and so that blue or ultraviolet curing light can be directed through the body of the transparent socket to cause initial tacking and bonding of the arch band at each tooth location.

After the arch bands 10, 10L and 10R have been positioned properly and the adhesive 42 has cured, the flexible handle applicator 60 is removed, by unsnapping the head portions from each socket. Next, as shown in FIG. 1, the intermaxillary fixation wires 18, 20, 22 and 24 are routed around groups of ligature studs, and the fixation wires are initially tightened. Additionally, a transfracture wire 86 is looped around the shank portions of studs 88 and 90 that project from the end portions of the lower arch bands 10R and 10L, respectively. The intermaxillary fixation wires and the transfracture wire are tightened from time-to-time as the left jaw segment 16 is manually guided toward the fracture line. The wire loops become smaller and smaller until the jaw segments are substantially reduced. Other combinations or configurations of studs and intermaxillary fixation wires can be utilized to obtain proper alignment and reduction of the fracture segments.

After an appropriate term of healing and recovery, the intermaxillary fixation wires and transfracture wires are cut, removed from the studs, and the arch bands are debonded from the patient's teeth. Preferably, one or more of the ligature studs are captured and gripped between the jaws of a debonding forceps, for example as shown in FIGS. 5 and 6. The retainer plugs 44 and retainer caps 46 provide a mechanical interlock with the arch band that has a greater strength than the bond strength of the hybrid cement 42 with the tooth enamel. Since the bonding strength of the hybrid cement is established at an intermediate level, for example at sixteen megapascals, the arch band along with substantially all of the underlying hybrid cement can be stripped away from the tooth enamel simply by applying appropriate torque forces through one or more of the ligature studs, for example as shown in FIGS. 5 and 6. Thus, debonding is easily accomplished without powered hand tools. Any cement residue remaining on the teeth can be easily removed manually with a conventional dental scaler.

It will now be appreciated that the arch band of the present invention substantially simplifies and improves the direct bonding attachment of a dental splint assembly to a patient's teeth for the restoration and healing of maxillo-mandibular injuries, including the reduction and temporary fixation of teeth, teeth rows and jaw segments. The symmetrical construction of the arch band and the ligature studs accommodates transfracture wires as well as conventional intermaxillary fixation wires which are essential for achieving reduction and fixation. Moreover, the symmetrical stud design permits universal coupling engagement with installation and debonding tools.

The symmetrical stud construction of the present invention also permits intermaxillary and transfracture forces to be applied by wires routed around two or more studs in any direction. That is, the arch band construction of the invention permits multiple wires to be routed in various directions to reduce a fracture, to bring broken bone segments together and to bring teeth into the maximum intercuspation position often without additional surgical procedures. For example, according to conventional practice with conventional arch bars, it is often necessary to make an incision in the gum tissue down to the jaw bone, and then dissect all of the soft tissue away from the bone until the fracture is exposed. It is then sometimes necessary to drill a hole on either side of the jaw bone for establishing sockets for receiving forceps that apply pressure toward the fracture site so that reduction can be achieved. The ligature stud construction of the present invention renders such procedures unnecessary, since intermaxillary fixation wires and transfracture wires can be routed from one arch band to another in various directions and around various stud combinations, thus making reduction possible without the application of special reduction forceps directly to bone.

Although the invention h as been described with reference to certain exemplary embodiments, it is to be understood that the forms of the invention shown and described are to be treated as preferred embodiments. Various changes, substitutions and modifications can be realized without departing from the spirit and scope of the invention as defined by the appended claims.

What is claimed is:

1. A dental arch band for use in connection with reconstructive oral surgery comprising a substantially flat body of bendable material and multiple ligature studs projecting from the body, each ligature stud including a shank portion attached to the body and a head portion attached to the shank portion, wherein the shank portion of at least one stud is tapered inwardly from the head portion to the arch band.

2. A dental arch band for use in connection with reconstructive oral surgery, the arch band having a facial side surface and a back side surface, and including multiple ligature studs attached to the arch band and projecting from the facial side surface with at least one ligature stud including a shank portion and a head portion with the shank portion being tapered inwardly from the head portion, the arch band being intersected by multiple openings that permit the flow or extrusion of bonding cement through the arch band, with the bonding cement when cured forming a retainer plug in at least one of the openings and a retainer cap overlapping the facial side surface bordering at least one of the openings.

3. A dental arch band system for use in connection with reconstructive oral surgery comprising:
   a dental arch band having a plurality of ligature studs each having a head portion; and
   a forceps tool of the type including gripping jaws and coupling pockets formed within the gripping jaws, wherein the head portion is conformed for capture and rotational mating engagement within the coupling pockets thereby permitting gripping engagement as well as rotational movement of the forceps tool relative to the ligature studs, whereby forces applied by a forceps tool during installation and removal of the dental arch band can be directed through a range of angles relative to the stud without inadvertent disengagement of the forceps tool from the head portion.

4. Dental splint apparatus intended for direct adhesive bond attachment to teeth during reconstructive oral surgery, comprising an arch band having a facial side surface, a back side surface for contacting dental cement, and the arch band being intersected by multiple openings that permit the flow or extrusion of bonding cement through the arch band; multiple ligature studs projecting from the facial side surface; and, a deposit of dental cement contacting the back side surface when the arch band is pressed against a patient's teeth, the dental cement consisting of glass ionomer mixed with a light-curable resin, the glass ionomer and resin being present in proportions that yield a bond strength in the range of from about eight megapascals to about twenty megapascals, with the dental cement when cured forming a retainer plug in at least one of the openings.

5. A dental splint for direct cement bonding attachment to the teeth of a patient for fixing and immobilizing the patient's jaw during and following oral surgery, comprising, in combination:
   an arch band made of a bendable material having a facial side surface and a back side surface for contacting a deposit of bonding cement; and,
   a plurality of ligature studs projecting from the facial side surface of the arch band, each stud including a shank portion for engaging a ligature wire and a head portion for engaging a forceps tool, wherein the shank portion of each stud is tapered inwardly from the head portion to the arch band.

6. A dental splint as set forth in claim 5, wherein the arch band is intersected by multiple apertures forming flow passages that open through the back side surface and the facial side surface, thereby permitting bonding cement contacting the back side surface to flow or extrude through the open flow passages onto the facial side surface when the arch band is pressed against a patient's teeth.

7. A dental splint as set forth in claim 5, wherein the arch band comprises a body of interlocking metal links with mesh passages formed between the interlocking metal links, thereby permitting bonding cement contacting the back side surface to flow or extrude into the mesh passages when the arch band is pressed against the patient's teeth.

8. A dental splint as set forth in claim 5, wherein the arch band comprises a substantially flat, rectangular body having a thickness dimension of from about 0.2 mm to about 0.6 mm, a length dimension of from about 8 cm to about 10 cm, and a width dimension of from about 3 mm to about 6 mm.

9. A dental splint as set forth in claim 5, wherein the ligature studs are formed as integral portions of the arch band.

10. A dental splint as set forth in claim 5, wherein the ligature studs are attached to the arch band by a weld union.

11. A dental splint as set forth in claim 5, wherein the ligature studs are attached to the arch band by a solder union.

12. A dental splint as set forth in claim 5, wherein the arch band comprises a rectangular body of metal selected from the group consisting of titanium and stainless steel.

13. A dental splint as set forth in claim 5, wherein the arch band and the ligature studs are formed as integral portions of a molded plastic material.

14. A dental splint as set forth in claim 5, wherein the arch band and the ligature studs are machined from a block of metal stock.

15. A dental splint as set forth in claim 5, wherein the shank portion of each stud is conical.

16. A dental splint as set forth in claim 5, wherein the head portion of each stud is conformed for capture within pockets formed within the beaks of a forceps tool.

17. A dental splint as set forth in claim 5, wherein the head portion of each stud is conformed for insertion into the coupling socket of an installation tool.

18. A dental splint as set forth in claim 5, wherein the head portion of each stud is hemispherical.

19. A dental splint as set forth in claim 5, wherein the head portion of each stud is cylindrical.

20. A dental splint as set forth in claim 5, wherein the head portion of each stud is dome-shaped.

21. A dental splint as set forth in claim 5, wherein the shank portion of each stud has a longitudinal axis, and the head portion of each stud is symmetrically formed with respect to the longitudinal axis.

22. A dental splint as set forth in claim 5, wherein the arch band comprises a substantially flat body having a longitudinal axis of symmetry, and the ligature studs are disposed on and spaced apart along the longitudinal axis of symmetry.

23. A dental arch band for use in connection with reconstructive oral surgery, wherein said dental arch band is operable to be bonded to a row of teeth by bonding cement so that a plurality of ligatures may engage said dental arch band and thereby act upon the row of teeth, said dental arch band comprising:

an arch band having a facial side surface and a back side surface, said arch band having a plurality of passages that permit a flow of the bonding cement through said arch band; and a plurality of ligature connections operable to be engaged by the plurality of ligatures, each of said ligature connections tapered inwardly to draw said ligatures against said arch band.

24. The dental arch band as defined in claim 23 wherein said plurality of passages form passages that extend from said facial side surface to said back side surface, whereby upon securing said arch band with the bonding cement, the bonding cement flows from said back side surface through said arch band to said facial side surface.

25. The dental arch band as defined in claim 24 wherein the bonding cement passing through said arch band produces multiple retainer plugs around said plurality of passages, said retainer plugs mechanically interlock and strengthen a bond between said arch band and the bonding cement.

26. The dental arch band as defined in claim 23 wherein said plurality of ligature connections are separate securing members that are secured to said facial side surface of said arch band.

27. The dental arch band as defined in claim 23 wherein said arch band is flexible and operable to be shaped to a surface to which said arch band is to be secured.

28. A method for securing a dental arch band for use in connection with reconstructive oral surgery, said method comprising:

providing an arch band having a facial side surface and a back side surface with a plurality of passages that permit a flow of bonding cement through the arch band;

applying bonding cement to at least one of the back side surface of the arch band and a row of teeth;

permitting the bonding cement to flow into at least a portion of the plurality of passages;

placing the back side surface of the arch band against the row of teeth;

applying a curing light to the bonding cement;

applying a plurality of ligatures to a plurality of ligature studs extending from said arch band; and tightening said plurality of said ligatures about inwardly tapered portions of the ligature studs, whereby said plurality of ligatures are pulled against the arch band to minimize sheer forces applied to the arch band.

29. The method for securing the dental arch band as defined in claim 28 further comprising thoroughly curing a plurality of retainer plugs formed by the bonding cement flowing out of the plurality of passages such that the retainer plugs provide a mechanical interlock between the arch band and the bonding cement.

30. A method for securing a dental arch band having a plurality of ligature connections to a row of teeth during reconstructive oral surgery, said method comprising:

providing a tool operable to engage substantially all of the plurality of ligature connections associated with the dental arch band at one time;

removably engaging substantially all of the plurality of ligature connections with the tool;

applying bonding cement to secure the arch band to the row of teeth;

positioning the arch band against the row of teeth using only the tool with substantially all of the plurality of ligature connections engaged by the tool;

applying a curing light to cure the bonding cement and to secure the arch band against the row of teeth; and disengaging the tool from the plurality of ligature connections associated with the dental arch band.

31. The method for securing a dental arch band as defined in claim 30 for an arch band having a plurality of studs extending therefrom, wherein removably engaging the plurality of ligature connections is performed by inserting each stud into press fit sockets formed into the tool and flexing the tool along with the arch band.

32. The method for securing a dental arch band as defined in claim 30 wherein removably engaging the plurality of ligature connections further includes removably engaging the plurality of ligature connections such that the dental arch band is curved to substantially conform to the row of teeth.

* * * * *